(12) United States Patent
Gray (10) Patent No.: US 8,221,097 B2
(45) Date of Patent: *Jul. 17, 2012

(54) ACTUATOR WITH GROOVED PISTON FOR A FLUID INFUSION DEVICE

(75) Inventor: John Gray, Woodland Hills, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 12/790,031

(22) Filed: May 28, 2010

(65) Prior Publication Data

US 2010/0232992 A1 Sep. 16, 2010

Related U.S. Application Data

(63) Continuation of application No. 11/253,822, filed on Oct. 18, 2005, now Pat. No. 7,753,660.

(51) Int. Cl.
*F04B 17/04* (2006.01)
*F04B 35/04* (2006.01)

(52) U.S. Cl. ............... 417/417; 417/555.1; 417/570; 92/162 P (58) Field of Classification Search ............ 417/417, 417/415, 416, 555.1, 570; 92/172, 174, 175, 92/181 R, 181 P, 162 P, 235–236
See application file for complete search history.

(56) References Cited

U.S. PATENT DOCUMENTS 5,509,792 A * 4/1996 Sullivan et al. ............. 417/417
6,805,693 B2 * 10/2004 Gray et al. ............. 604/891.1

FOREIGN PATENT DOCUMENTS

WO WO03/022328 A2 3/2003

OTHER PUBLICATIONS

European Patent Office, European Office Action for European Patent Application No. 06816858.2, Feb. 28, 2011.

* cited by examiner

*Primary Examiner* — Charles Freay
*Assistant Examiner* — Christopher Bobish
(74) *Attorney, Agent, or Firm* — Ingrassia Fisher & Lorenz, P.C.

(57) ABSTRACT

An apparatus for delivering a fluid includes a housing, an inlet in the housing for receiving the fluid, and an outlet in the housing for discharging the fluid. A piston channel is provided within the housing through which the fluid flows from the inlet to the outlet. An actuator is positioned within the housing and is moveable between a retracted position and a forward position, the actuator defining a piston chamber for storing fluid received through the inlet when the actuator is in the retracted position and for driving the fluid stored in the piston chamber toward the outlet when the actuator transitions from the retracted position to the forward position. The actuator includes an armature and a piston coupled to the armature and moveable within the piston channel. The piston is provided with a groove in an outer surface for conducting fluid from the inlet to the outlet.

7 Claims, 9 Drawing Sheets

ACTUATOR WITH GROOVED PISTON FOR A FLUID INFUSION DEVICE

CROSS-REFERENCE TO RELATED APPLICATIONS

This application is a continuation of U.S. patent application Ser. No. 11/253,822, filed Oct. 18, 2005.

TECHNICAL FIELD

This invention relates generally to infusion devices and, more particularly, to an actuator for use in an infusion device drive mechanism, the actuator being configured to facilitate periodic cleaning of the infusion device and to generally improve fluid flow from the infusion pump's inlet reservoir to the pump's outlet chamber.

BACKGROUND

Infusion devices may be used to deliver an infusion media (e.g. a medication such as insulin) to a patient. Such devices may be designed to be implanted into a patient's body to deliver predetermined dosages of the infusion media to a particular location within the patient's body; e.g. in the venous system, the spinal column, or within the peritoneal cavity.

A known infusion device of the type described above includes a drive mechanism that includes a reciprocating pumping element made of a ferrous material. The reciprocating pumping element includes an actuator including a piston portion that is coupled to an armature portion. The piston portion is configured to reciprocate within a piston channel when a solenoid coil is alternately energized and de-energized. That is, when the solenoid is energized, magnetic flux causes the actuator to move very quickly (i.e. in the order of 2-3 milliseconds) until it reaches a stop member. This corresponds to the pump's forward stroke and results in the delivery of a predetermined dosage of infusion media from an outlet chamber to the patient. When the solenoid is de-energized, the lack of magnetic flux allows the actuator to return to its original position under the force of a spring. This, in turn, causes the pressure in the piston chamber to fall. The reduced pressure in the piston chamber causes infusion media to flow from a reservoir through an annulus between the actuator piston and the piston cylinder wall to refill the piston chamber thus equalizing the pressure between the reservoir and the piston chamber and preparing the pump for its next pumping or delivery stroke. This is referred to as the refill stroke. The annulus between the actuator piston and the piston cylinder is very small (i.e. in the order of 150 to 250 microinches radially) resulting in an outlet chamber refill process that takes between about 1 to 2 seconds. In contrast, the pump's forward (delivery) stroke may be approximately 500 times faster than the refill process.

Over time, protein drugs such as insulin denature resulting in the deposition of protein on the surfaces of fluid paths; for example, on the surfaces that form the annulus between the actuator piston and the pistol cylinder. Such deposits may cause valves to leak, impede the motion of moving parts, and/or otherwise degrade device performance. Typically, such deposits are removed periodically (e.g. once per year) by rinsing the implanted pump with a solvent (for example, sodium hydroxide (NaOH)) causing the deposits to dissolve.

The rinsing procedure is typically performed as follows. The infusion device's reservoir is first filled with a desired buffer or rinsing solution. Since the device is implanted near the patient's skin, the reservoir may be filled utilizing a first syringe. A second syringe engages the device's outlet to produce a negative pressure differential and therefore help pull the fluid through the pump. The pump itself is operated during this procedure to assist fluid flow through the pump. In the case of insulin, it is an established goal that the rinsing procedure should result in the transport of at least 1 cc of rinsing fluid from the inlet reservoir to the pump's outlet in approximately ten minutes. Rinse cycles less than ten minutes in duration may result in failure to dissolve all deposits, and rinse cycles greater than ten minutes may result in undue discomfort to the patient. The rinse procedure may include a multi-stage operation that involves emptying and refilling the pump's reservoir several times with different fluids, and different drug therapies may require the use of different rinsing agents. It is to be understood that other protein drugs may require different rinse times and/or volumes.

As previously stated, the space or annulus between the surface of the actuator piston and the piston cylinder wall is approximately 150-200 micro-inches radially, a fairly tight fit, and it takes approximately 1 to 2 seconds to refill the piston chamber via this annulus. Deposits of the type described above that form on the annulus walls will restrict fluid flow thus increasing the time it takes to refill the piston chamber, which, in turn, lowers the stroking frequency and causes the corrective rinse procedure to be protracted; e.g. it could take 30 minutes or more instead of the desired 10 minutes. The deposit build-up could be so extreme so as to cause the pump to jam. In this case, it could take more than 30 minutes to pass ¼-½ cc of rinsing fluid. This may not be sufficient to render the pump operational.

BRIEF SUMMARY

According to an aspect of the invention, there is provided an apparatus for delivering a fluid. The apparatus includes a housing, an inlet in the housing for receiving the fluid, an outlet in the housing for discharging the fluid, a piston channel within the housing through which the fluid flows from the inlet to the outlet, and an actuator positioned within the housing and moveable between a retracted position and a forward position. The actuator in conjunction with the piston channel defines a piston chamber for storing fluid received through the inlet when the actuator is in the retracted position. The actuator drives the fluid stored in the piston chamber toward the outlet when the actuator transitions from the retracted (or refill) position to the forward (or delivery) position. The actuator includes an armature and a piston coupled to the armature and moveable within the piston channel. The piston has a groove in an outer surface for conducting fluid from the inlet to the outlet.

According to a further aspect of the invention, there is provided an actuator for delivering fluid through a piston channel from an inlet to an outlet. The actuator includes an armature configured to move between a forward position and a refracted position, and a piston that is coupled to the armature and moveable within the piston channel. The piston has a groove in an outer surface for conducting fluid through the groove.

According to a still further aspect of the invention, there is provided an actuator mechanism including an armature portion and a piston portion coupled to the armature portion and having a groove in an outer surface thereof.

BRIEF DESCRIPTION OF THE DRAWINGS

Embodiments of the present invention will hereinafter be described in conjunction with the following drawings wherein like reference numerals denote like elements throughout.

DETAILED DESCRIPTION OF THE INVENTION

The following detailed description is of the best presently contemplated mode of implementing the invention. This description is not to be taken in a limiting sense, but is merely for the purpose of illustrating the general principles of embodiments of the invention. Furthermore, there is no intention to be bound by any theory presented in the preceding background of the invention or the following detailed description of the invention. The scope of the invention is best defined by the appended claims.

As discussed above, embodiments of the present invention relate to an infusion device and to a drive mechanism including an actuator that improves fluid flow from the device's inlet reservoir to the device's outlet and facilitates the periodic cleaning of the device.

Figure 1:
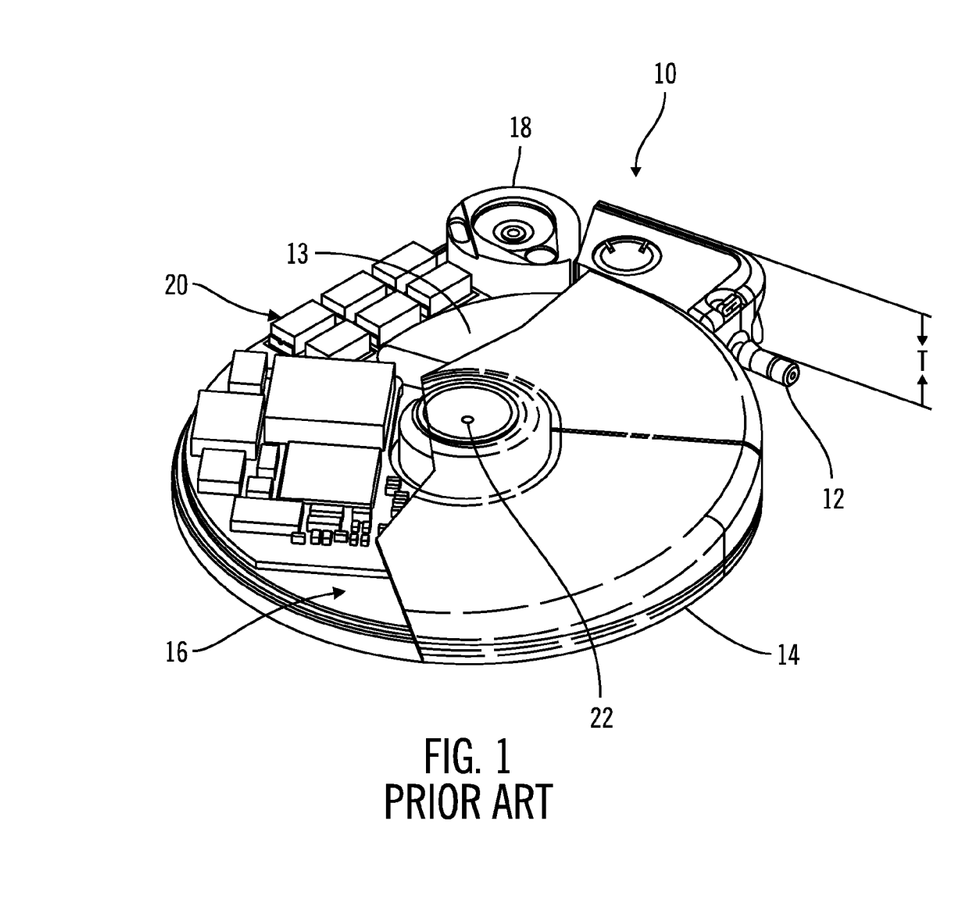
FIG. 1 is an isometric view of an implantable infusion device in accordance with the prior art.

FIG. 1 shows an implantable infusion device 10 in accordance with the teachings of the prior art. The illustrated device 10 is configured to be surgically implanted into a patient, for example, in the abdominal region, between the skin and the abdominal wall. A catheter connected to the pump may deliver infusion medium to the patient, for example, by feeding infusion medium to a particular location in the venous system, within the spinal column, or in the peritoneal cavity of the patient. As described below, embodiments of the device 10 are configured in accordance with one or more aspects of the invention for enhancing prolonged usage and cleaning after implantation. However, further embodiments of the invention may be implemented as external infusion devices, which connect to patients through suitable catheter devices or the like. Yet further embodiments of the invention may be used in other contexts; e.g. for delivery of a medium into other suitable environments. Therefore, for purposes of simplifying the present disclosure, the term "patient" is used herein to refer to any environment in which an implantable device is implanted or to which an external device is connected, whether or not the implant or connection is carried out for medical purposes. Also, the term "infusion medium" is used herein to refer to any suitable medium delivered by the drive device.

The device 10 includes a generally disc-shaped housing 14. While a generally circular disc-shaped embodiment is illustrated in FIG. 1, it will be understood that further embodiments of the invention may employ housing of other shapes, including, but not limited to, oval, oblong, rectangular, or other curved or polygonal shapes. In implantable devices, the housing 14 is made of a biocompatible material and most often has a relatively small diameter and thickness to reduce patient trauma during implant surgery and after implantation.

The housing 14 includes a reservoir 16 for holding a volume of infusion medium, such as, but not limited to, a liquid medication to be administered to the patient. Housing 14 also contains a drive mechanism 18 (e.g. a pump), a power source 13, and control electronics 20 described below. Pump 18 is configured to receive infusion media from reservoir 16 via a pump inlet 22. Inlet structure 22 provides a closeable and sealable fluid flow path to the reservoir in the reservoir portion of the housing. The inlet structure includes a port for receiving a needle through which fluid may be transferred to the infusion device; for example, to fill or re-fill the reservoir of the device with the infusion media or a rinsing fluid as will be more fully discussed below. In particular embodiments, the inlet structure is configured to re-seal after a fill or re-fill operation, and to allow multiple re-fill and re-seal operations. One example of an inlet structure is described in U.S. Pat. No. 6,652,510, titled "Infusion Device and Reservoir for Same," which is incorporated herein by reference. However, further embodiments may employ other suitable inlet structures, including, but not limited to, those described in U.S. Pat. Nos. 5,514,103 and 5,176,644, each to Srisathapat et al.; U.S. Pat. No. 5,167,633 to Mann et al.; U.S. Pat. No. 4,697,622 to Swift; and U.S. Pat. No. 4,573,994 to Fischell et al. Representative examples of reservoir housing portions and reservoirs which may be employed in embodiments of the invention are described in the above referred to U.S. Pat. No. 6,652,510, and further embodiments may employ other suitable reservoir configurations, including, but not limited to, those described in the above referred to U.S. Pat. Nos. 5,514,103; 5,176,644; 5,167,633; 4,697,622; and 4,573,994.

Returning now to FIGS. 1 and 2, pump 18 has an outlet 24 through which the infusion medium may be expelled. When the device 10 is implanted in a patient or connected externally to a patient, a catheter 12 may be connected to the outlet 24 to deliver expelled infusion medium into the patient's blood stream or to a selected location in the patient's body.

The infusion device 10 includes a drive mechanism 18 such as a pump, and an electronic control system 20 located in the housing portion 14. The drive mechanism 18 is connected between the reservoir and the outlet of the infusion device. The electronic control system 20 includes a power source 13, such as a battery, and control electronics for controlling the drive mechanism 18 to deliver infusion medium from the reservoir to the patient in a prescribed manner. The drive mechanism may be controlled to deliver infusion medium in any suitable manner; for example, according to a programmed dispensing rate or schedule or according to an actuation signal from a sensor, timer or other suitable source.

In particular embodiments, both the drive mechanism 18 and the reservoir 16 are hermetically sealed. In such embodiments, the housing 14 containing drive mechanism 18 and control electronics 20 may be made from titanium or titanium alloy or other biocompatible metals, while the reservoir portion 16 of the housing may be made from such metals or a biocompatible and infusion medium compatible plastic as long as the material is such as to permit the required hermetically.

The drive mechanism 18 includes mechanical and electromagnetic components that inhabit a volume of space within the housing 14 in which the components reside and operate. In that regard, the drive mechanism can contribute to the thickness requirements of the housing 14, and thus to the overall thickness of the device 10. The ability to reduce or minimize the device thickness without compromising the drive capabilities can provide significant advantages with respect to patient comfort, appearance and flexibility in selecting implant locations of the body. In particular embodiments, the drive mechanism 18 is configured to have a relatively small thickness thus allowing the device 10 to have a relative small thickness. Also in particular embodiments, the device 10 is configured such that, once implanted, it functions for a relatively long period of time to administer infusion medium to the patient to periodically be replenished from the outside of patient's body, and to be periodically rinsed to remove unwanted protein build-up on the fluid path surfaces that may degrade the performance of the infusion device.

Figure 2:
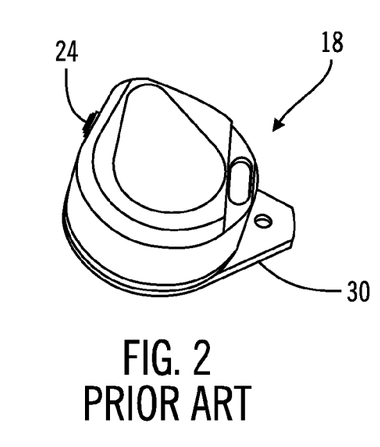
FIG. 2 is an isometric view of a drive mechanism for the implantable infusion device shown in FIG. 1.

FIG. 2 illustrates a drive mechanism 18 in accordance with the prior art. The drive mechanism 18 has a partially cylindrical, disc-shaped configuration having an inlet 30 and an outlet 24. The inlet 30 may be coupled in fluid communication with reservoir 16 of device 10 (FIG. 1) through a suitable conduit (not shown) within the device 10. Similarly, the outlet 24 may be coupled in fluid communication with outlet 12 of the device 10 in FIG. 1, through a suitable conduit (not shown) within the device 10.

Figure 3:
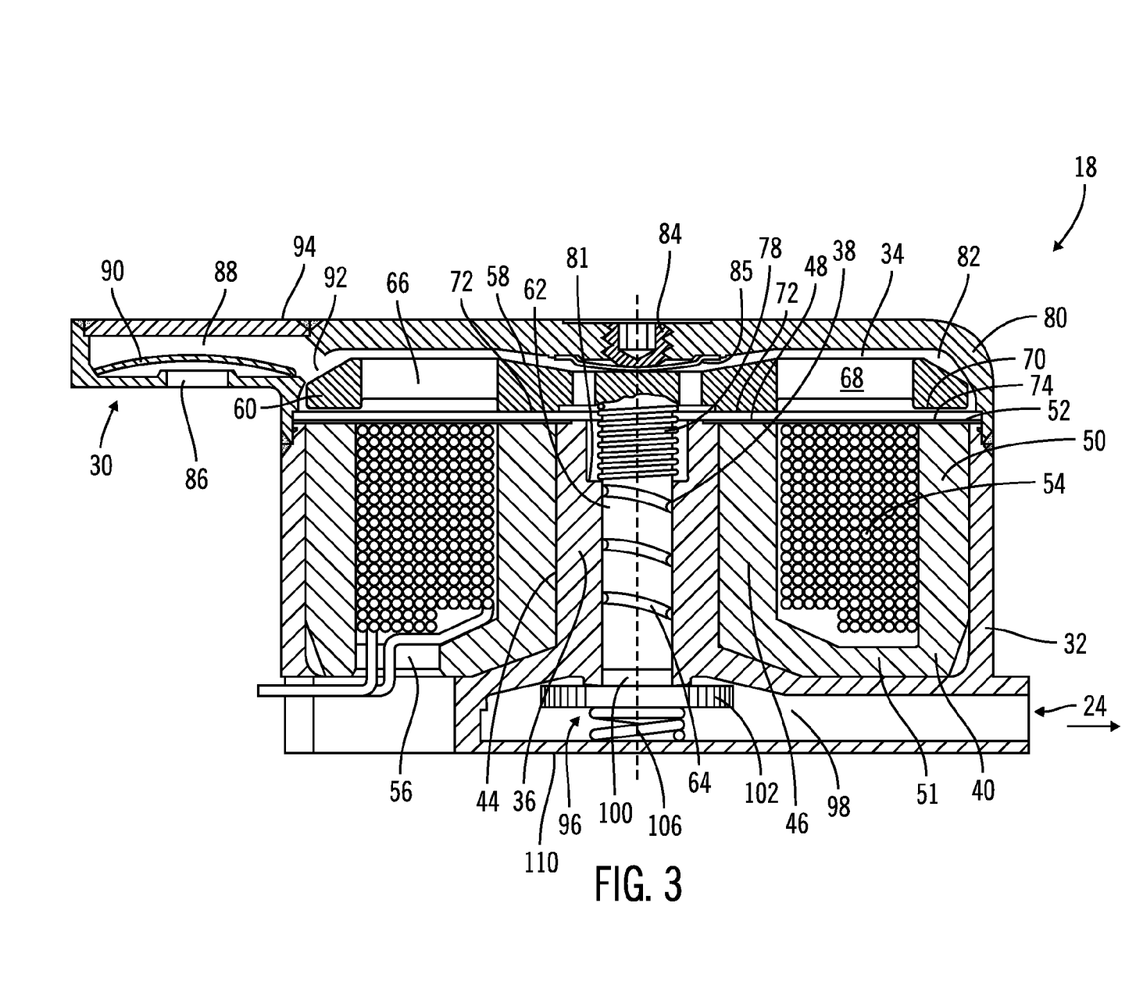
FIG. 3 is a cross-sectional view of a drive mechanism in accordance with a first embodiment of the present invention.

FIG. 3 is a cross-sectional view of a drive mechanism 18 in a retracted position or state in accordance with an embodiment of the present invention. As described in more detail below, the drive mechanism 18 employs electromagnetic and mechanical forces to change (or move) between retracted and forward states to cause infusion medium to be drawn in through the inlet 30 and forced out of the outlet 24, respectively. The assembly of components shown in FIG. 3 is also shown in an exploded view in FIG. 4.

Figure 4:
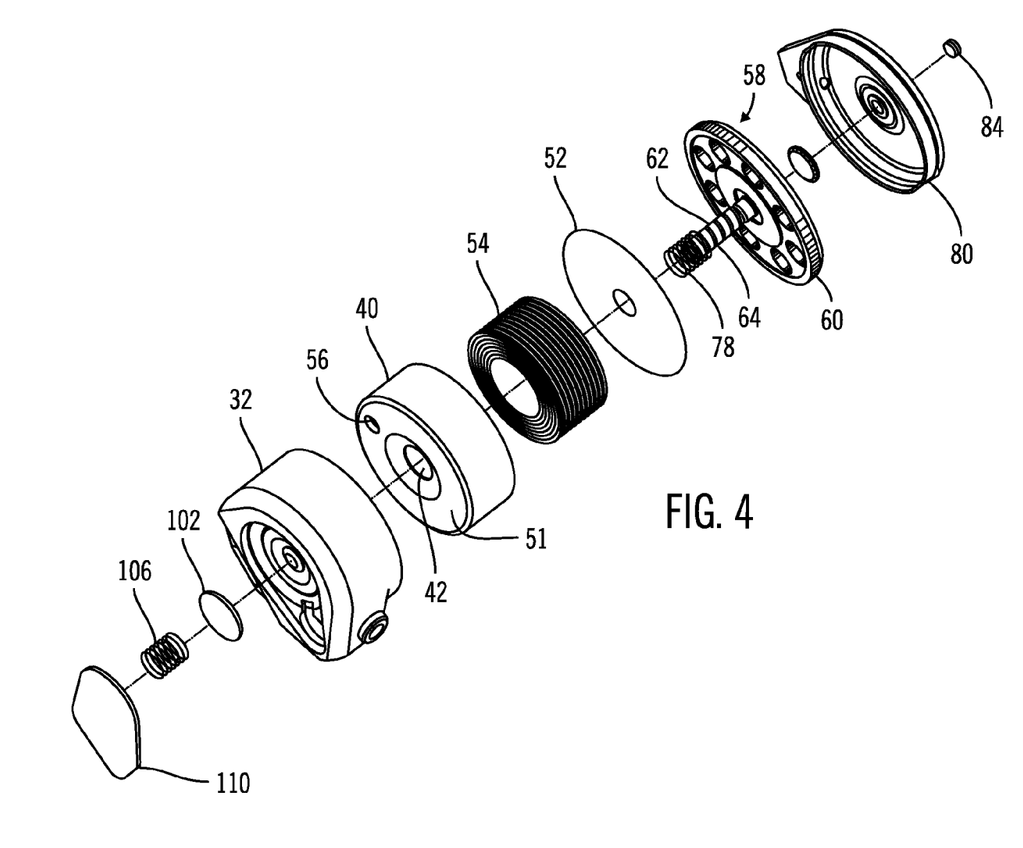
FIG. 4 is an exploded view of an embodiment of the drive mechanism shown in FIG. 3.

Referring to FIGS. 3 and 4, the drive mechanism 18 includes a housing member 32 that is open on one side to a hollow, annular interior section 34. The housing 32 has a central hub portion 36 with a central piston channel 38. The bottom side of the housing member 32 (with reference to the orientation shown in FIG. 3) includes an opening to the hollow interior section 34 through which coil wires may pass, as described below. The bottom side of the housing member also includes a configuration of recesses and cavities for providing an outlet chamber and an outlet passage. The housing member 32 is most often made of generally rigid, biocompatible and infusion medium compatible material having no or low magnetic permeability such as, but not limited to, titanium, stainless steel, biocompatible plastic, ceramic, glass or the like.

As shown in FIGS. 3 and 4, a coil cup 40 is located within the annular interior section 34 of the housing 32. The coil cup 40 has a generally cylinder shape, open on one side to a hollow, annular interior. The coil cup 40 includes a bore 42 located in a central hub portion 44 and extending axially relative to the annular interior. The hub portion 44 of the cup member defines an inner annular wall 46 having an end surface 48 (or inner pole surface) having a width $W_1$. The cup member 40 has an outer wall 50 having an end surface 52 (or outer pole surface) having a width $W_2$. The outer wall 50 is connected to the inner wall 46 of hub portion 44 by a backiron portion 51 of the cup member 40. As described in further detail below, at the open end of cup member 40, the end surfaces 48 and 52 of the inner and outer walls 46 and 50, respectively, define pole surfaces that cooperate with pole surfaces on an armature to provide a path for electromagnetic flux during a forward stroke of the drive mechanism. In particular embodiments, the width $W_1$ of inner pole surface 48 is greater than the width $W_2$ of the outer pole surface 52 to provide certain electromagnetic characteristics as described below.

When assembled, the coil cup 40 is located in the hollow interior of the housing member 32, with the central portion 36 of the housing 32 extending through channel 42 of the coil cup 40 as shown in FIG. 3. A coil 54 is located within the hollow, annular interior of the coil cup 40 and is disposed around the axis of the annular interior of the coil cup 40. The coil cup 40 is provided with an opening 56 through which coil leads extend, as shown in FIGS. 3 and 4. The coil cup 40 is most often made of generally rigid material having a relatively high magnetic permeability such as, but not limited to, low carbon steel, iron, nickel, ferritic stainless steel, ferrite, other ferrous materials, or the like. The coil 54 includes a conductive wire wound in a coil configuration. The coil wire may include any suitable conductive material such as, but not limited to, silver, copper, gold or the like, with each turn electrically insulated from adjacent turns and the housing. In one particular embodiment, the coil wire has a square or rectangular cross-section to achieve minimal space between windings and a greater number of coil turns thus improving electrical efficiency.

Figure 5:
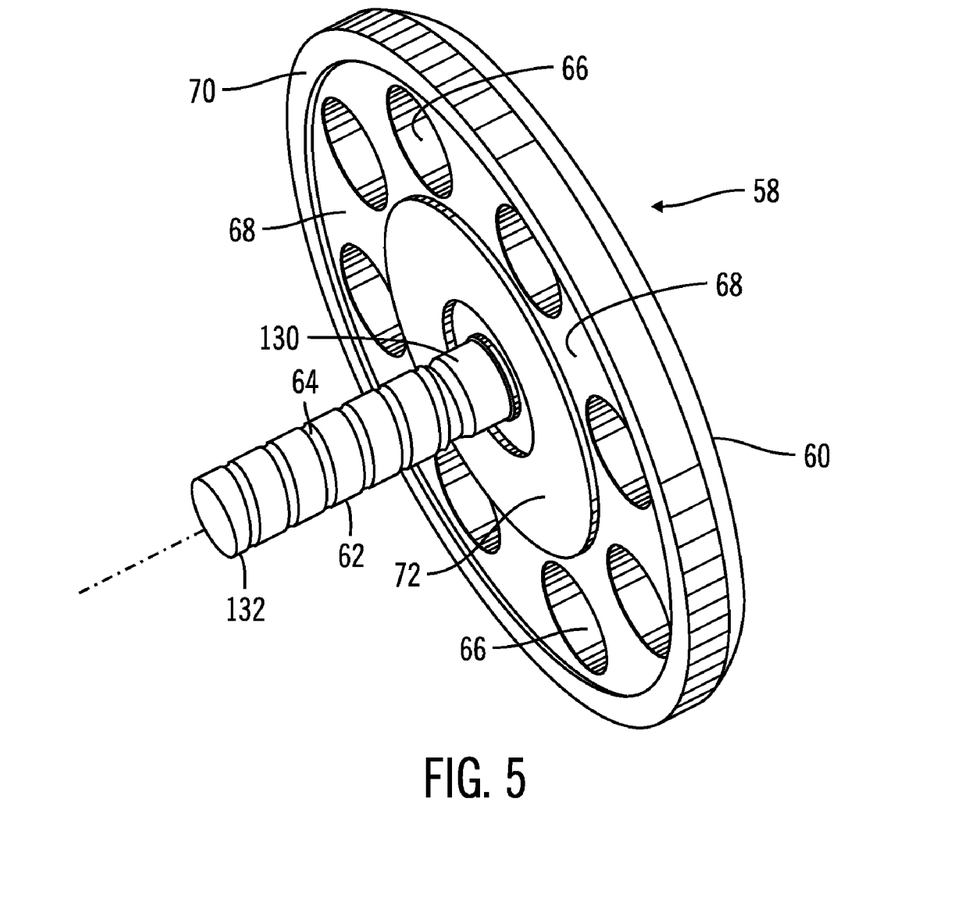
FIG. 5 is an isometric view of an embodiment of an actuator including an armature and a grooved piston for use in the drive mechanism shown in FIGS. 3 and 4.

The drive mechanism 18 also includes an actuator member 58, which has an armature portion 60 and a piston portion 62. The actuator member is most often made of a generally rigid, biocompatible and infusion medium compatible material having a relatively high magnetic permeability such as, but not limited to, ferrous materials, ferritic stainless steel with high corrosion resistance, or the like. In the embodiment of FIGS. 3, 4, and 5, the actuator (with an armature portion 60 and a piston portion 62) is formed as a single, unitary structure. In other embodiments as described below, the piston portion may be a separate structure with respect to the armature portion.

A perspective view of the example actuator member 58 is shown in FIG. 5, where the armature portion 60 of the actuator member has a round, disc shape, and may be provided with at least one opening, and most often a plurality of openings as shown in the drawing. The openings in the illustrated example include a plurality of substantially circular openings 66. The sections 68 of the armature 60 between openings 66 generally define radial struts coupling an annular outer section (or outer pole) 70 to an inner section (or inner pole) 72 of the armature. In particular embodiments, the width $W_1$ of the inner pole surface is greater than the width $W_2$ of the outer pole surface corresponding to the difference between the width of the pole surface 48 on the inner wall 46 of the cup member and the width of the pole surface 52 on the outer wall 50 of the cup member.

As described in more detail below, the armature 60 cooperates with the inner and outer walls of the coil cup 40 to provide a flux path for electromagnetic flux. The spacing between the pole surfaces on the armature 60 and the pole surfaces on the coil cup walls define gaps in the flux path. In particular embodiments, the spacing between the surface of outer pole 70 of the armature 60 and the surface of outer pole 52 of the outer wall 50 of the coil cup 40 (or a barrier 74 described below) is greater than the spacing between the surface of inner pole 72 of the armature and the pole surface 48 of the inner wall 46 of the coil cup (or the barrier 74) when the actuator is in the retracted position shown in FIG. 3.

The radial struts 68 in the armature provide radial paths for electromagnetic flux between the outer and inner pole sections 70 and 72 of the armature. The openings 66 provide a passage for infusion medium to pass as the actuator 58 is moved between retracted and forward stroke positions to reduce resistance to the actuator motion that the infusion medium may otherwise produce. The configuration of openings is most often designed to provide a sufficient conductor for electromagnetic flux and yet minimize or reduce viscous resistance to actuator motion. With reference to FIG. 3, the actuator member 58 is arranged with the piston portion 62 extending through the axial channel 38 of the housing 32 and with the armature portion 60 positioned adjacent to the open side of the coil cup 40. An actuator spring 78 is positioned to force the armature portion 60 of the actuator 58 in the direction away from the open side of the coil cup 40 to provide a gap between the armature 60 and the open side of the coil cup 40. A biocompatible and infusion medium compatible barrier 74 is located over the open side of the coil cup 40 between the armature 60 and the coil cup 40 to help seal the annular interior of the coil cup 40 and coil 54. In other embodiments in which infusion medium may contact the coil, the barrier 74 may be omitted.

The actuator spring 78 in the illustrated embodiment includes a coil spring disposed around the piston portion 62 of the actuator 58 adjacent the armature portion 60. One end of the coil spring abuts the armature portion 60 of the actuator, while the opposite end of the coil spring abuts a shoulder 81 in the piston channel 38 of the housing 32. In this manner, the actuator spring 78 imparts a spring force between the housing and the actuator 58 to urge the actuator toward its retracted position shown in FIG. 3.

In the illustrated embodiment, by using a coil spring 78 located around and coaxial with the piston portion 62 and disposed partially within the piston channel 38, the actuator spring may have minimal or no contribution to the overall thickness dimension of the drive mechanism. However, in other embodiments, actuator springs may have other suitable forms and may be located in other positions suitable for urging the actuator toward its retracted position shown in FIG. 3. The actuator spring 78 is most often made of a biocompatible and infusion medium compatible material that exhibits a suitable spring force such as, but not limited to, titanium, stainless steel, MP35N cobalt steel or the like.

The drive mechanism 18 further includes a cover member 80 which attaches to the housing member 32 over the open side of the housing member and the barrier 74. The cover member 80 is most often made of a generally rigid, biocompatible and infusion medium compatible material having a relatively low magnetic permeability (being relatively magnetically opaque) such as, but not limited to, titanium, stainless steel, biocompatible plastic, ceramic, glass or the like.

The cover member 80 defines an interior volume 82 between the barrier 74 and the inner surface of the cover member. The armature portion 60 of the actuator member 58 resides within the interior volume 82 when the cover is attached to the housing below, the armature 60 is moveable in the axial direction within the volume 82 between a retracted position shown in FIG. 3 and a forward stroke position. This movement is created by the action of electromagnetic force generated when a current is passed through the coil 54 and the mechanical return action of the actuator spring 78.

An adjusting plunger 84 is located within the cover 80 for contacting the armature 60 when the armature is in the fully retracted position shown in FIG. 3 to set the retracted position of the armature. In particular embodiments, a seal (e.g. a silicon rubber sealing ring) may be disposed between the plunger 84 and the cover member 80. In further embodiments, a flexible diaphragm 85 (such as, but not limited to, a thin titanium sheet or foil) may be coupled to the inside surface of the cover 80 and sealed around the opening through which the plunger 84 extends. The diaphragm will flex to allow the plunger to define an adjustable retracted position and, yet, provide sealing functions for inhibiting leakage at the interface between the plunger 84 and the cover 80. In other embodiments, after a proper armature position is set, the plunger is fixed in place with respect to the cover member, for example, by adhering the plunger to the cover member with one or more welds, adhesives or other securing methods.

The cover member 80 includes the inlet 30 of the drive mechanism, which has an inlet opening 86 in fluid flow communication with the interior volume 82 as described below. The inlet opening 86 connects in fluid flow communication with the reservoir of the infusion device 10 (FIG. 1) to receive infusion medium from the reservoir. Connection of the inlet opening 86 and the reservoir may be through suitable conduit (not shown), such as tubing made of suitable infusion medium compatible material, including, but not limited to, titanium, stainless steel, biocompatible plastic, ceramic, glass or the like.

The inlet opening 86 provides a flow path to an inlet chamber 88 formed in the cover member 80 adjacent the inlet opening. A filter or screen member, such as a porous or screen material 90, may be disposed within the inlet chamber 88. The filter or screen member 90 is provided in a flow path between the inlet opening 86 and an inlet port 92 to the volume 82. A one-way inlet valve (not shown) may also be provided in the flow path between the inlet opening 86 and the inlet port 92 or within the inlet port 92 to allow medium to flow into but not out of the interior volume 82 through the inlet. The cover member 82 may be provided with an inlet cover 94 that, when removed, allows access to the inlet chamber 88 to, for example, install, replace or service a filter 90 or inlet valve, or to service or clean the inlet 86.

As shown in FIG. 3, the piston portion 62 of the actuator 58 extends through the axial channel 38 in the housing 32 toward an outlet chamber 98 at the end of the axial channel 38. The channel 38 has an inside diameter which is larger than the outside diameter of the piston portion 62. As a result, an annular volume is defined between the piston portion 62 and the wall of the axial channel 38 along the length of the axial channel 38. Infusion medium may flow through the annular volume 82 within the cover 80 to a piston chamber 100 located between the free end of the piston portion 62 and a valve member 102 of a valve assembly 96. In particular embodiments, the radial spacing between the piston portion 62 and the wall of the channel 38 is selected to provide a suitable flow toward the piston chamber 100 to refill the piston chamber 100 (during a return stroke of the piston portion), but small enough to sufficiently inhibit back flow of medium from the piston chamber 100 (during a forward stroke of the piston portion).

The actual radial spacing between the piston portion 62 and the wall of the channel 38 to achieve such results depends, in part, on the overall dimensions of those components, the pressure differentials created in the mechanism, and the viscosity of the infusion medium. In particular embodiments, the radial spacing is selected such that the volume of medium for refilling is between about 1 and 4 orders of magnitude (and, most often, about 2 orders of magnitude) greater than the volume of medium that back-flows through the space. Alternatively, or in addition, the radial spacing may be defined by the ratio of the diameter $D_P$ of the piston portion 62 to the diameter $D_C$ of the channel 38, where the ratio $D_P/D_C$ is most often within a range of about 0.990 to about 0.995. As a representative example, a total spacing of about 400 to 600 micro-inches and, most often, an average radial gap of about 250 micro-inches annularly around the piston portion 62 may be employed.

The valve assembly 96 in the embodiment of FIG. 3 includes the valve member 102 and a valve spring 106. The valve member 102 is located within the outlet chamber 98 and, as shown in FIG. 3, is positioned to close the opening between the axial channel 38 and the outlet chamber 98 when the actuator 58 is in the retracted position. During the forward stroke, the valve member 102 is positioned to open a flow passage between the axial channel 38 and the outlet chamber 98. The valve spring 106 is located within the outlet chamber 98 to support the valve member 102. The spring 106 imparts a spring force on the valve member 102 in the direction toward piston 62 urging the valve member 102 toward a closed position to block the opening between the axial channel 38 and the outlet chamber 98.

The valve member 102 is most often made of generally rigid, biocompatible and infusion medium compatible material, such as, but not limited to, titanium, stainless steel, biocompatible plastic, ceramic, glass, gold, platinum or the like. A layer of silicon rubber or other suitable material may be attached to the rigid valve member material on the surface facing the channel 38 to help seal the opening to channel 38 when the valve member is in the closed position shown in FIG. 3.

The valve spring 106 is most often made of biocompatible and infusion medium compatible material that exhibits a suitable spring force such as, but not limited to, titanium, stainless steel, MP35N cobalt steel or the like. In the illustrated embodiment, the valve spring 106 is a coil spring. In other embodiments, other suitable valve spring configurations may be employed, including, but not limited to, helical, flat, radial, spiral, barrel, hourglass, constant or variable pitch springs or the like.

The embodiment shown in FIG. 3 utilizes a valve cover 110 sealed to the housing 32 to enclose the outlet chamber 98. The valve cover 110 is most often made of a generally rigid, biocompatible and infusion medium compatible material, such as, but not limited to, titanium, stainless steel, biocompatible plastic, ceramic, glass, gold, platinum or the like.

The coil 54 may be inserted into the annular interior of the coil cup 40 with the coil leads extended through a coil lead opening 56 in the coil cup. The coil may be impregnated or partially impregnated with a fill material of epoxy or the like for adhering the coil to the coil cup and for sealing or partially sealing the coil. The fill material may also be used to adhere the barrier plate to the coil members to avoid warping or bulging of the barrier plate after assembly.

The coil cup 40 and the coil 54 may be inserted into the interior of the housing 32 with the coil leads (which may be wire leads or flexible conductive tabs) extending through a coil lead opening 56 in the housing 32. In particular embodiments, the coil cup and housing are configured to provide a tight friction fit that does not require additional means to adhere the two components together. In other embodiments, the coil cup 40 and housing 32 may be coupled together by a suitable adhesive material or other adhering methods, including, but not limited to, welding, brazing or the like.

The barrier 74 may be placed over the coil, coil cup and housing sub-assembly. The barrier 74 may be adhered to the housing by one or more adhering points or continuously secured along the circumference of the barrier 74 with any suitable adhesive material or other adhering methods, including, but not limited to, welding, brazing, soldering, or the like. Alternatively, or in addition, the barrier 74 may be held in place by a shoulder portion of the cover 80, as shown in FIG. 3. In addition, as noted above, the barrier 74 may be adhered to the coil 54 by fill material in the coil. In particular embodiments, the barrier 74 is held in a generally flat position relative to the coil cup and coil. To enhance this flat relationship, the coil cup and housing may be assembled together and then machined to planarize the barrier contact surfaces prior to inserting the coil in the coil cup and prior to adding fill material to the coil.

After the barrier 74 is placed over the coil, coil cup and housing, the actuator 58 may be added to the sub-assembly. First, however, the actuator spring 78 is placed around the piston portion 62 adjacent the armature portion 60 of the actuator. Then the free end of the piston portion 62 is passed through the axial channel 38 of the housing 32 with the armature end of the actuator arranged adjacent the barrier 74.

The cover member 80 may then be disposed over the armature end of the actuator and secured to the housing 32. In particular embodiments, the cover member 80 is adhered to the housing by one or more adhering points or continuously along the circumference of the cover member 80 with one or more welds or any other suitable adhering methods, including, but not limited to, adhesive materials, brazing or the like. The inlet filter 90 and the inlet cover 94 may be pre-assembled with the cover member 80 prior to adding the cover member to the sub-assembly. Alternatively, the filter 90 and the inlet cover 94 may be added to the cover member 80 after the cover member 80 is assembled onto the housing 32. In particular embodiments, the filter 90 is disposed within the inlet chamber 88 and then the inlet cover 94 is adhered to the cover member 80 by one or more adhering points or continuously along the circumference of the inlet cover with one or more welds or any other suitable adhering methods, including, but not limited to, adhesive materials, brazing or the like.

The valve side of the drive mechanism may be assembled before or after the above-described components are assembled. On the valve side of the drive mechanism, the valve member 102 is disposed within the outlet chamber cavity 98 of the housing 32 adjacent the opening to the axial channel 38. The valve spring 106 is then disposed within the outlet chamber cavity 98 adjacent the valve member 102. The valve cover 110 may then be placed over the outlet chamber cavity 98. In particular embodiments, the valve cover 110 is adhered to the housing 32 by one or more adhering points or continuously along the circumference of the valve cover with one or more welds or any other suitable adhering methods, including, but not limited to, adhesive materials, brazing or the like.

The volume of piston chamber 100, the compression of the actuator spring 78, and the position of the actuator 58 in the retracted position shown in FIG. 3 may be adjusted by adjusting the position of the adjusting plunger 84. In one particular embodiment, the adjusting plunger includes a threaded cylindrical member that engages corresponding threads in a plunger aperture in the cover member 80 to allow adjustment in a screw-threading manner. The diaphragm 85 under the plunger 84 contacts the armature portion 60 of the actuator inside of the cover member 80. The other end of the plunger 84 may be provided with a tool-engagement depression for allowing engagement by a tool, such as a screw-driver, Allen wrench or the like, from outside of the cover member 80. By engaging and rotating the plunger 84 with a suitable tool, the depth that the plunger extends into the cover member 80 may be adjusted to adjust the refracted position of the armature portion 60 relative to the barrier 74 (to adjust the gaps between the pole sections 70 and 72 of the armature and pole sections formed by the coil cup 40 when the actuator is in the retracted position of FIG. 3). In one particular embodiment, adjustments of the plunger 84 are made during manufacture. In that embodiment, the adjusted position is determined and set by welding or otherwise adhering the plunger 84 in the adjusted position during the manufacture. In other embodiments, the plunger 84 is not set and welded during manufacture to allow adjustment of plunger 84 after manufacture.

Figure 6:
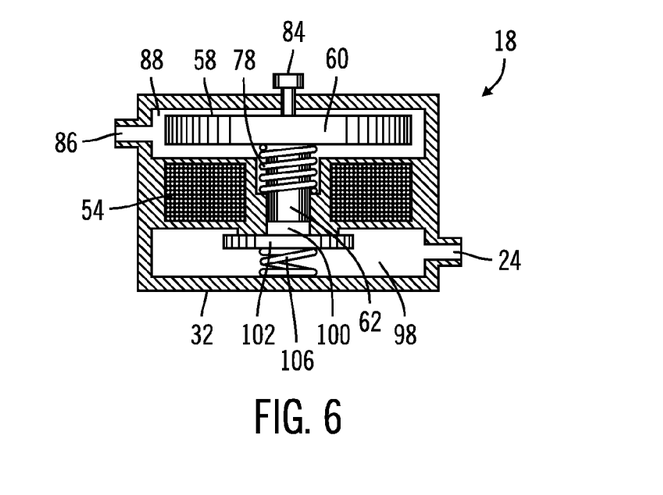
FIGS. 6, 7, and 8 are simplified cross-sectional views of the drive mechanism shown in FIG. 3 in quiescent, forward, and retracted states, respectively.
Figure 7:
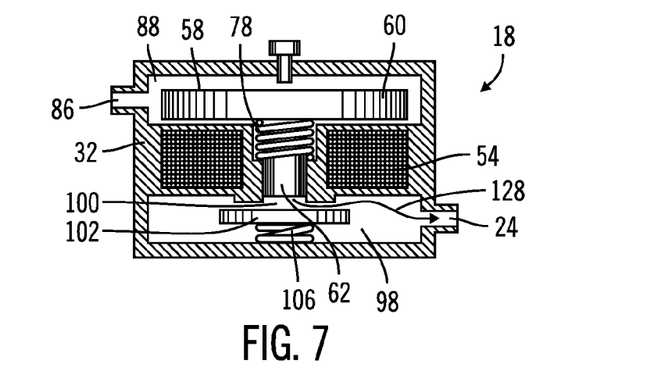
Figure 8:
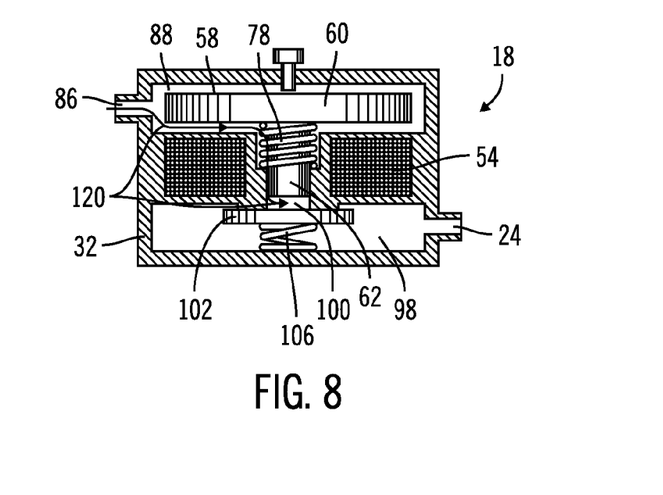

FIGS. 6, 7 and 8 are simplified cross-sectional views of the drive mechanism 18 shown in FIG. 3 and will be useful in explaining the operation of drive mechanism 18. In the interest of clarity, only major functional features and components are illustrated, and these are identified by reference numerals corresponding to reference numerals used in FIG. 3 to denote like features and components.

FIG. 6 illustrates drive mechanism 18 in its quiescent state. That is, valve member 102 is fully extended under the force of spring 106, piston chamber 100 and inlet chamber 88 are substantially filled with infusion media (or rinsing media as the case may be), and coil 54 is de-activated (not energized or inadequately energized) in a manner to overcome the force of spring 78. Drive mechanism 18 employs electromagnetic and mechanical forces to move between retracted (FIG. 8) and forward (FIG. 7) positions to cause infusion medium to be drawn into and driven out of the mechanism in a controlled manner. In the retracted position, the spring 78 urges the actuator 58 toward its retracted position shown in FIG. 8. When the coil 54 is energized to overcome the spring force of spring 78, the actuator 58 moves to its forward stroke position shown in FIG. 7. The movement of the actuator between retracted and forward positions creates pressure differentials within the internal chambers and volumes of the drive mechanism 18 to draw medium into the inlet 86 and drive medium out the outlet 24.

More specifically, when the coil 54 is de-activated, the actuator 58 is held in its retracted position (FIGS. 6 and 8) under the force of the spring 78. When coil is de-activated immediately following a forward stroke, the spring 78 moves the actuator 58 to the retracted position of FIG. 8 from the forward position shown in FIG. 7. The openings 66 (FIG. 5) in the armature portion 60 of the actuator 58 provide passages for medium to pass and, thus, reduce viscous drag on the actuator. As a result, the actuator 58 may move to its retracted position (FIG. 8) relatively quickly.

As the actuator 58 retracts, the piston portion 62 of the actuator is retracted relative to the valve member 102 such that a piston chamber 100 volume is formed between the end of the piston portion 62 and the valve member 102. The formation of the piston chamber 100 volume creates a negative pressure which draws infusion medium (or rinsing fluid) from the volume 82 of the cover member 80 through the annular space between the piston portion 62 and the wall of the channel 38 and into the piston chamber 100 as is indicated by arrows 120. While not shown, one or more channels could be provided through the piston portion 62 to provide one or more additional flow paths to the piston chamber 100 if desired.

In the retracted position, a gap is formed between each of the annular pole surfaces 48 and 52 defined by the inner and outer walls 46 and 50 of the coil cup 40 and respective annular surfaces of the inner and outer pole sections 72 and 70 of the actuator's armature portion 60. With particular reference to FIG. 3, a first gap is formed between the annular pole surface 48 of the inner cup member wall 46 and the annular surface of the inner pole section 72. A second gap is formed between the annular surface 52 of the outer cup member wall 50 and the annular surface of the outer pole section 70.

When the coil 54 is energized in a manner to overcome spring force 78, the actuator 58 is forced in the direction to close the gaps and moves to its forward position (FIG. 7) under the influence of electromagnetic flux generated by the energized coil. In particular, the coil may be energized by passing an electrical current through the coil conductor to create electromagnetic flux. The electromagnetic flux defines a flux path through the coil cup walls across the gaps and through the armature portion of the actuator. The electromagnetic flux provides an attraction force between the annular surfaces 48 and 52 of the coil cup 40 and the annular surfaces of the armature's pole sections 70 and 72 to overcome the spring force of spring 78 and draw the armature 60 toward the coil cup.

As the armature portion 60 of the actuator is drawn toward the coil cup 40, the piston portion 62 of the actuator is moved axially through the channel 38 in the direction toward the outlet chamber 98. With the coil energized, the piston portion 62 continues to move under the action of the armature until a mechanical stop is reached, for example, mechanical contact of the actuator 58 with the barrier 74, a portion of the housing 32 or cover member 80. In other embodiments, the motion may continue until the return force of the spring and fluid pressure overcomes the electromagnetic force provided by energizing the coil.

The movement of the piston portion 62 towards the stopping point reduces the volume of the piston chamber 100 and increases the pressure within the piston chamber until the pressure is sufficient to overcome the force of the valve spring 106. As the valve spring force is overcome by the pressure within the piston chamber, the valve member 102 is moved toward an open position, away from the opening between the piston chamber 100 outlet chamber 98. When the valve member 102 is in the open position, medium is discharged through the outlet chamber 98 and outlet 24 as is indicated by arrow 128 in FIG. 7.

When the coil is deactivated and the piston portion 62 is moved back to its retracted position, the pressure in the piston chamber 100 reduces and the valve member 102 is reseated under the action of the valve spring 106. This prevents fluid from flowing back into the drive mechanism through the outlet. In addition, a negative pressure is created in the piston chamber 100 to draw medium into the chamber for the next forward stroke, as described above.

In this manner, energization of the coil 54 to move the actuator 58 to its forward position (FIG. 7) causes a measured volume of medium to be discharged from the outlet. As described above, when the coil 54 is de-energized, the actuator 58 is returned to the retracted position (FIG. 8) under the force of spring 106 and an additional volume of medium is drawn into the piston chamber 100 for the next discharging operation. Accordingly, the coil 54 may be energized and de-energized by a controlled electronic pulse signal where each pulse may actuate the drive mechanism 100 to discharge a measured volume of medium. In particular embodiments, the coil 54 may be electrically coupled to an electronic control circuit (not shown) to receive an electronic pulse signal from the control circuit; for example, in response to a sensor signal, timer signal or other control signal input to the control circuit.

In particular embodiments, when the piston motion is stopped at the end of the forward stroke, the valve-facing end of the piston portion 62 is in close proximity to the valve member 102, for example, spaced from the valve member 102 by a distance that is no more than two to three percent (2-3%) of the piston diameter. In further embodiments, the valve facing end of the piston portion 62 is in contact with the valve member 102 at the end of the forward stroke. In this manner, gas that may be present in the infusion medium is less likely to accumulate within the piston chamber 100. More specifically, in some operational contexts, infusion medium may contain gas in the form of small bubbles that may migrate into the piston chamber 100 during filling of the piston chamber. As gas is significantly more compressible than liquid, too much gas within the piston chamber may adversely affect the ability of the drive mechanism to self prime.

In yet another embodiment, the piston portion 62 may contact the valve member 102 at the end of the forward stroke and push the valve member 102 open. In this embodiment, it is less likely that gas will be trapped between the piston portion 62 and the valve member 102 and more likely that the chamber will be purged of gas.

As already described, protein drugs such as insulin denature resulting in the deposition of denatured protein on the surfaces of the fluid delivery path. Over time, such deposits may (1) occlude the delivery path to the therapy site; (2) reduce clearances between moving parts and thus slow operation and perhaps ultimately cause jamming; (3) compromise the condition of valve mating surfaces causing the valve not to seat properly; and (4) create areas of precipitant coagulation that may grow and collect debris thus further impacting fluid flow and device operation.

These deposits may be periodically removed (e.g. once per year) by rinsing the implanted pump with a solvent (e.g. sodium hydroxide) to dissolve the deposits. The infusion device's reservoir is first filled with a desired buffer or rinsing solution. Since the device is implanted near the patient's skin, the reservoir may be filled utilizing a first syringe. A second syringe engages the device's outlet to produce a negative pressure differential and therefore help pull the fluid through the pump. The pump itself may be operated during this procedure to assist fluid flow through the pump. It is an established goal that the rinsing procedure should result in the transport of at least 1 cc of rinsing fluid from the inlet reservoir to the pump's outlet in approximately ten minutes. Rinse cycles less than ten minutes in duration may result in failure to dissolve all deposits, and rinse cycles greater than ten minutes may result in undue discomfort to the patient. The rinse procedure may include a multi-stage operation that involves emptying and refilling the pump's reservoir several times with different fluids, and different drugs may require the use of different rinsing agents. However, other time periods may be used depending on the agent used, the frequency between rinsings, the amount of deposits and/or the like.

As previously stated, the space or annulus between the actuator piston and the piston cylinder is approximately 150-200 micro-inches radially, a fairly tight fit, and it takes approximately 1 to 2 seconds to refill the piston chamber via the annulus. Deposits on the annulus walls, however, will restrict fluid flow thus increasing the time to refill the piston chamber, which, in turn, lowers the stroking frequency and causes the corrective rinse procedure to be protracted; e.g. it could take 30 minutes or so instead of the desired 10 minutes. The deposit build-up could be so severe so as to cause the pump to jam. In this case, it could take more than 30 minutes to pass ¼-½ cc of rinsing fluid and thus may not be sufficient to render the pump operational.

Figure 9:
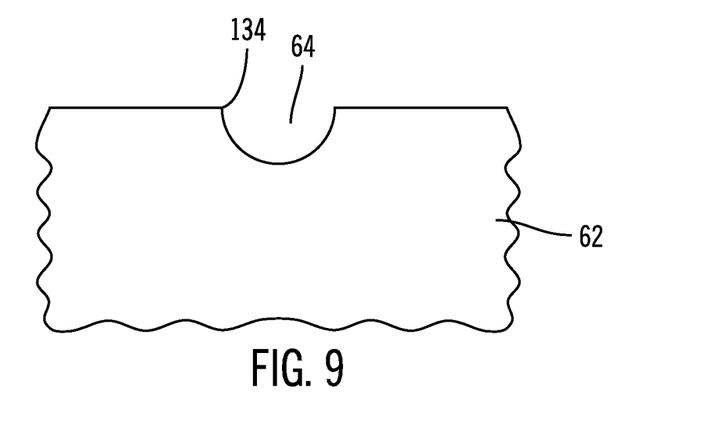
FIGS. 9, 10, and 11 are cross-sectional views of three piston grooves in accordance with an embodiment of the present invention.

To overcome these problems and provide a more effective flow path for the rinsing agent, a groove is provided in the outer surface of the actuator piston. For example, actuator piston 62 is provided with a helical groove 64 and is shown in FIGS. 3 and 5. Groove 64 may have, for example, a hemispherical cross-section as shown in FIG. 9 of sufficient cross-sectional area to ensure that a flow path will always exist regardless of the amount of deposits in the bore from the inlet end 130 of actuator piston 62 to the outlet end 132 of actuator piston 62. In addition, the helical groove 64 is most often configured to deliver rinsing agent in close proximity to any protein deposit in the annulus between the actuator piston 62 and the surface of the central piston channel 38. In this manner, rinsing agent can be effectively applied to deposits even when the actuator is jammed.

In particular, groove 64 is configured to conduct rinsing agent to within approximately 0.015 inch of any deposit in the annulus. To this end, it has been found that for devices of this nature, a groove having a depth that is approximately 1.5-6% of the diameter of the piston, a width that is approximately 3-30% of the diameter of the piston, a pitch that is approximately 8-70% of the diameter of the piston, and/or a cross-sectional area that is approximately 0.2-0.6% of the area of the piston face is helpful. More specifically, a groove having a width of substantially 0.012 inch, a depth of substantially 0.0035 inch, and a pitch of about 0.025-0.035 inch works quite well. In this case, the groove 64 will have approximately seven turns. More specifically, the groove may have 1-2 turns in the area occupied by piston spring 78 and 5-6 turns in the remainder of the piston 62. It will be appreciated that a tight spiral path (i.e. many turns) makes it more certain that the rinsing agent will reach deposits in the annulus; however, too many turns could result in back leakage during the pumping stroke due to the corresponding reduction in the piston's regions of higher diameter which are responsible for the piston's tight fit within the piston channel. It is to be noted, however, that since the forward stroke is very fast (e.g. 1.5 milliseconds) and the refill time is much longer (e.g. 100-150 times longer), the back leakage is dramatically smaller than the forward flow. Furthermore, a helical groove of the type shown in FIG. 5 causes fluid flow to transition from laminar to turbulent thereby restricting fluid flow. Thus, the groove generally provides a flow path when the actuator is moving relatively slowly (retracting) and provides a sealing action when the actuator is moving fast (pumping).

Figure 10:
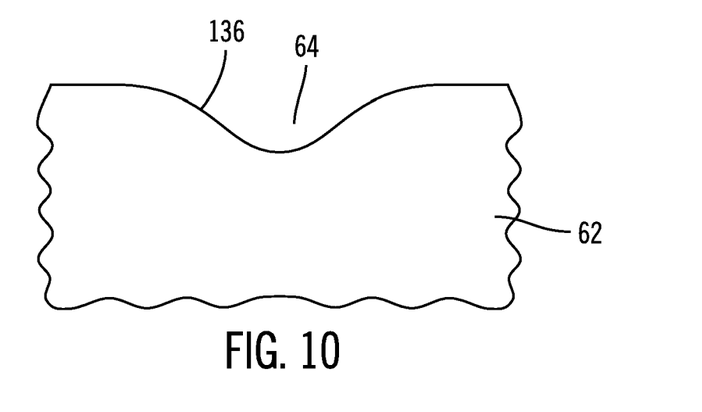
Figure 11:
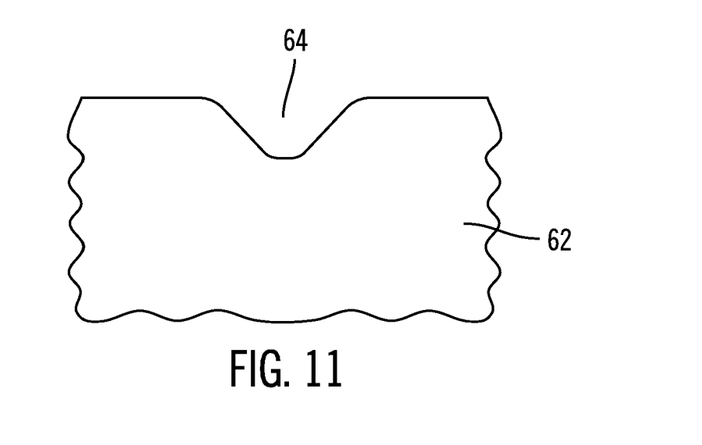

While the groove in the outer surface of the actuator piston is shown in FIG. 9 as having a hemispherical cross-section, it is known that sharp edges in the flow path (such as edges 134 in FIG. 9) may cause further denaturing of the protein therapy drug. Therefore, in a particular embodiment shown in FIG. 10, groove 64 has a cross-sectional shape including rounded edges 136. It should be clear, however, that grooves having a variety of cross-sectional shapes may be employed depending on the particular application and circumstances, and all such grooves are considered to be within the scope of the present invention. For example, groove 64 shown in FIG. 11 includes rounded edges for the reasons described above, but has a cross-section that is generally more conical.

Groove 64 enhances the operation of drive mechanism 18 in several ways. First, it can assure that a flow path will exist between the pump's inlet 86 and outlet 24 even if there are heavy protein deposits on the surfaces of the flow path. This permits rinsing agent to pass through the mechanism even if the mechanism is jammed. Second, it can significantly shorten the refill period by 75 percent or more compared to that of a smooth, ungrooved actuator of similar dimensions thus increasing the amount of rinsing agent that may be pumped by the actuator. Under normal operation, the increased frequency of operation permits infusion rates to be increased thus permitting therapy drugs to be delivered to the patient more expeditiously.

Figure 12:
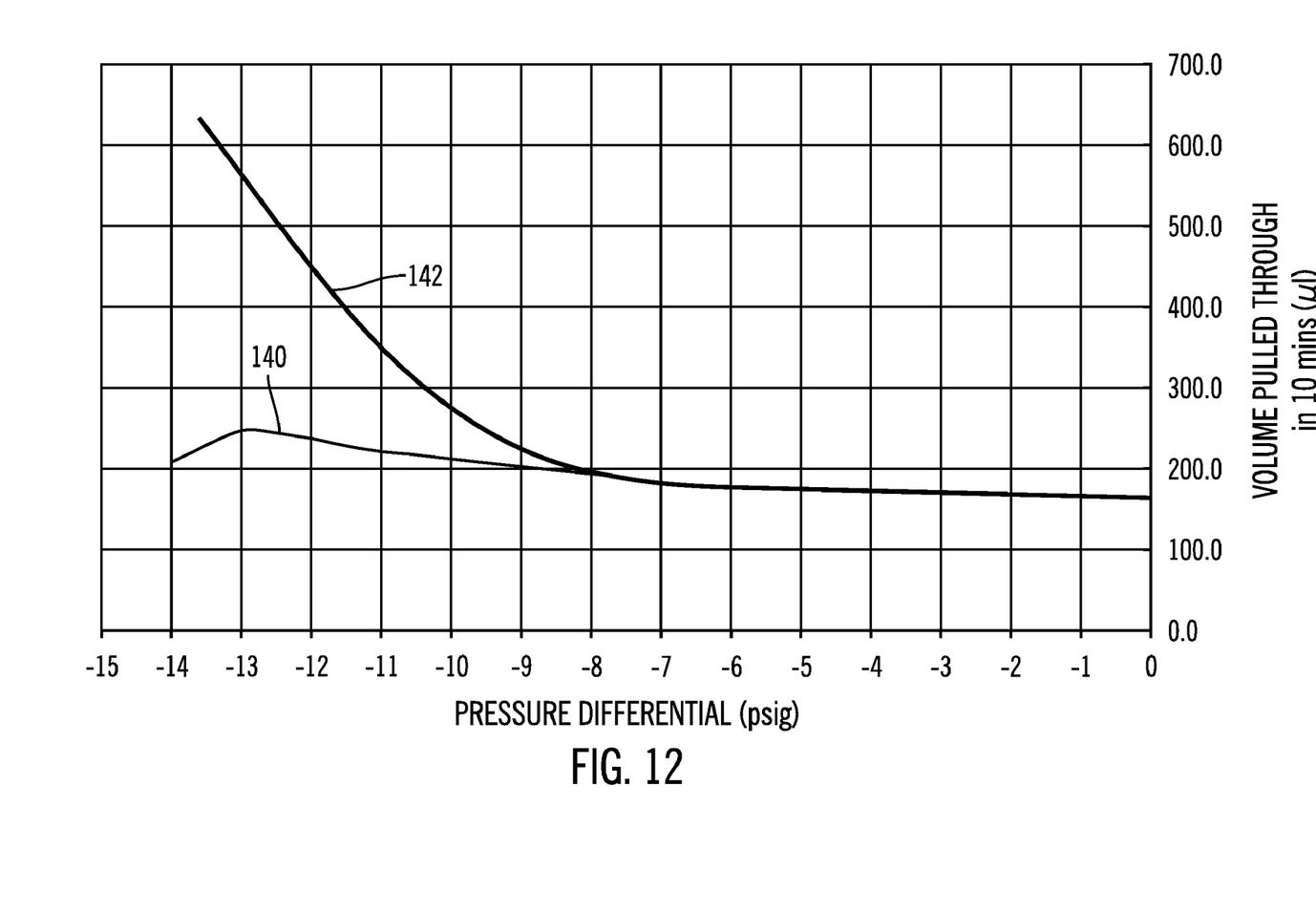
FIG. 12 is a graph illustrating the relationship between pressure differential and volume pull-through for grooved and ungrooved actuator pistons.

The graph shown in FIG. 12 illustrates the relationship between the inlet-to-outlet pressure differential (horizontal axis) and the volume of fluid pulled through a pump in ten minutes (vertical axis) for a drive mechanism having a smooth actuator (curve 140) and an actuator including a seven-turn helical groove having a width of approximately 0.01 inch and a depth of 0.004 inch in the surface thereof (curve 142). As can be seen, at pressure differentials greater than −8 psig, the volume pull-through in the grooved actuator increases dramatically above that of the smooth actuator. In fact, at a differential pressure of −13 psig, the pull-through of the grooved actuator is over two times that of the ungrooved actuator. If the pump is operated while the differential pressure is applied, the volume passed through the pump will exceed 1 cc in 10 minutes.

Figure 13:
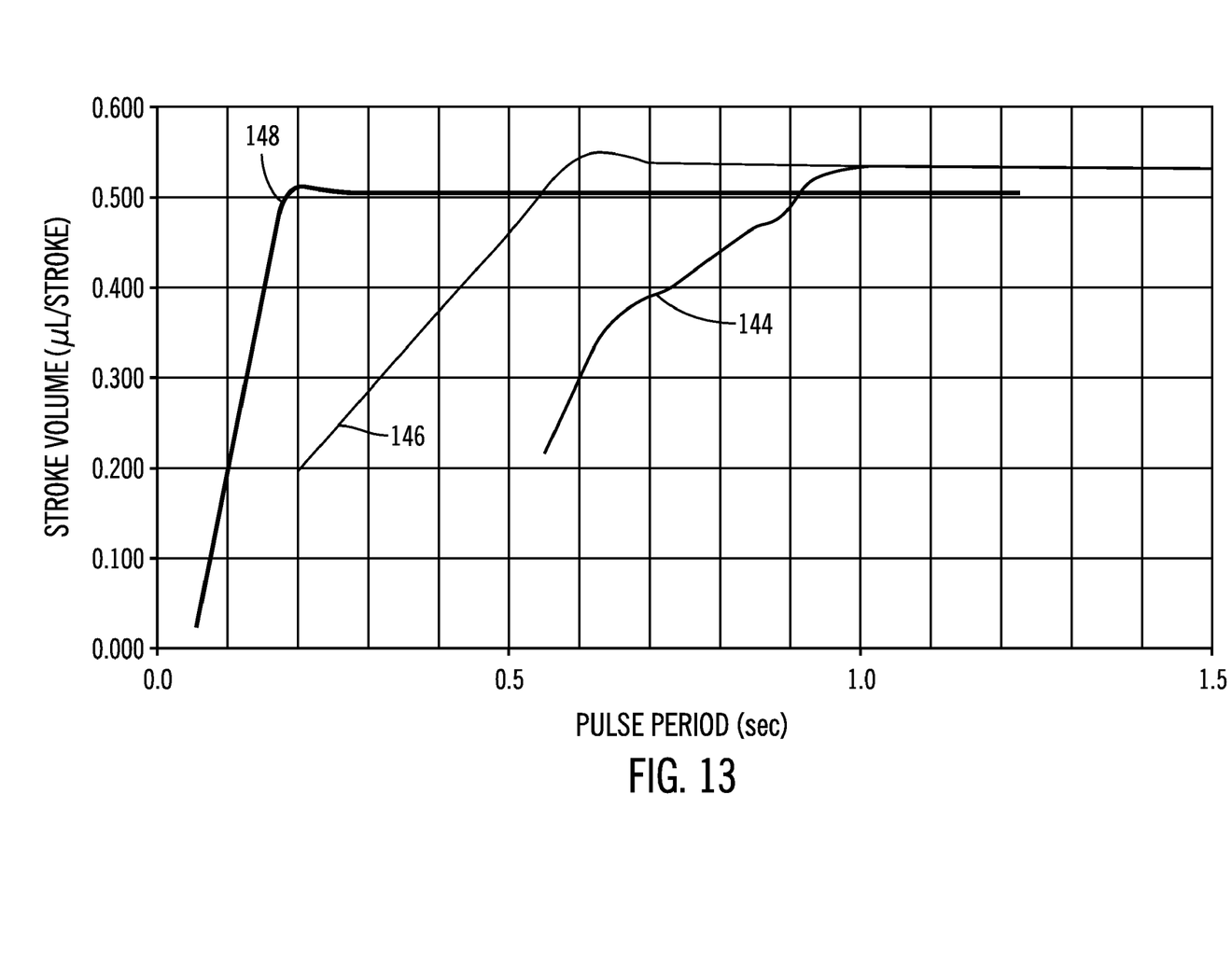
FIG. 13 is a graph illustrating the relationship between stroke volume and pulse period for grooved and ungrooved actuator pistons.

FIG. 13 illustrates the relationship between stroke refill volume (vertical axis) and pump pulse period (horizontal axis) for a standard ungrooved actuator (curve 144), an actuator having a 0.0025 inch deep helical groove in its surface (curve 146), and an actuator having a 0.004 inch deep helical groove therein (curve 148). As can be seen, the stroke refill volume for the ungrooved actuator peaks at about 1.0 second, and the actuator with the 0.0025 inch deep helical groove therein peaks at about 0.6 second. The actuator having the 0.004 inch deep helical groove therein has a stroke refill volume that peaks in about 0.2 second, approximately five times faster than the ungrooved actuator piston. Thus, an infusion pump equipped with the grooved actuator piston characterized by curve 148 in FIG. 13 can be operated at approximately five times the speed of a pump having an ungrooved actuator piston.

Figure 14:
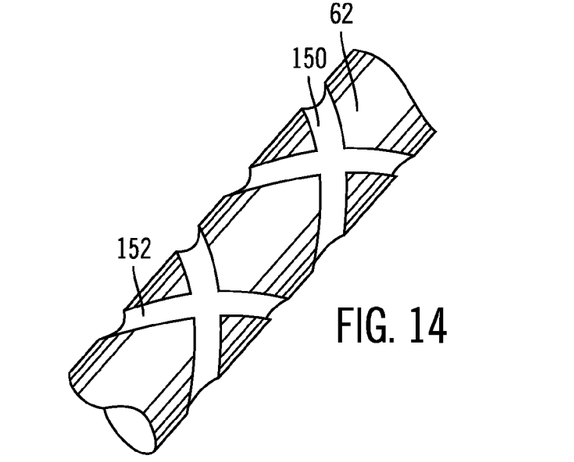
FIG. 14 is an isometric view of a portion of an actuator piston having first and second oppositely directed helical grooves.
Figure 15:
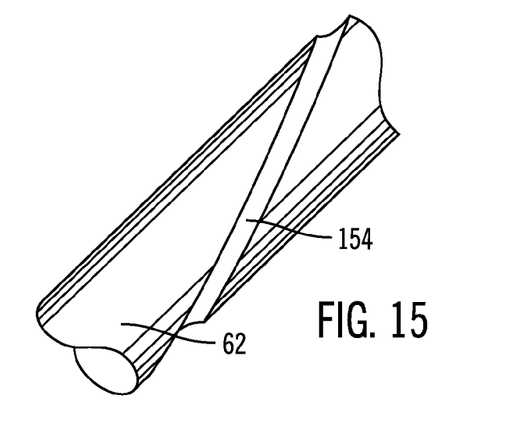
FIG. 15 is an isometric view of a portion of an actuator piston having a helical groove with very few turns.
Figure 16:
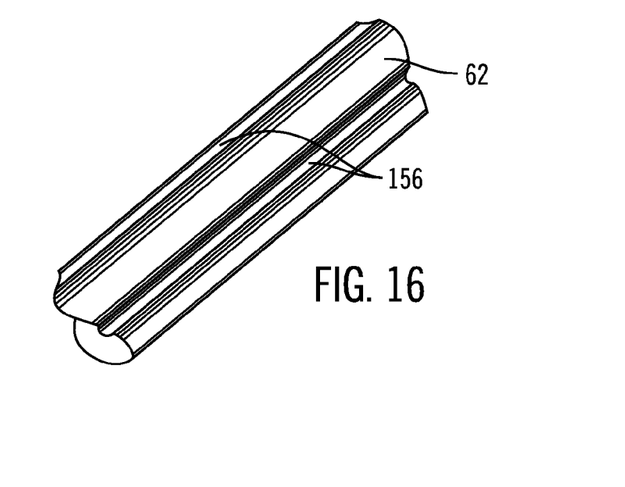
FIG. 16 is an isometric view of a portion of an actuator piston having a plurality of longitudinal straight grooves.

Thus far, the inventive drive mechanism/actuator has been described in accordance with particular embodiments; i.e. one in which the actuator piston has a helical groove in the surface thereof. It should be appreciated, however, that different configurations and/or numbers of grooves may be utilized. For example, FIG. 14 illustrates an actuator piston 62 that includes a double helical groove formed by a right-spiral groove 150 and a left-spiral groove 152. The use of two or more grooves such as is shown in FIG. 14 may permit the grooves to be shallower and still provide the desired results. FIG. 15 illustrates a helical groove 154 including a lesser number of turns, perhaps less than one turn, and FIG. 16 illustrates an actuator piston 62 having one or more straight grooves 156 in its surface. While reducing the number turns or utilizing straight grooves may result in increased back leakage during the forward stroke of the piston, the forward stroke (pumping) of the piston will still be substantially faster than the rearward stroke (refill) and the back leakage will still be substantially less that the forward flow. Finally, one or more such grooves may be provided in the cylinder wall to facilitate fluid flow as described above in connection with the groove or grooves in the armature piston.

Thus, there has been provided an infusion pump that dispenses predetermined dosages of a protein drug (e.g. insulin) and is configured to facilitate the passage of rinsing fluid to remove undesirable protein building on the fluid path surfaces. The infusion pump includes a piston pumping mechanism that includes an actuator configured to dissolve protein build-up on the surfaces of the piston and piston walls. In addition, the drive mechanism is configured to reduce the time it takes to refill the outlet chamber of the infusion pump to an acceptable time despite the build-up of protein deposits on the walls of the pump's fluid path.

While at least one exemplary embodiment has been presented in the foregoing detailed description of the invention, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient road map for implementing exemplary embodiments of the invention, it being understood that various changes may be made in the function and arrangement of elements described in an exemplary embodiment without departing from the scope of the invention as set forth in the appended claims and their legal equivalents.

What is claimed is:

1. An actuator mechanism for a hermetically sealed implantable fluid infusion device having a piston channel, a first fluid chamber above the piston channel, and a second fluid chamber below the piston channel, the actuator mechanism comprising:
    an armature that moves between a forward position and a retracted position to facilitate delivery of fluid from the first fluid chamber to the second fluid chamber via the piston channel;
    a piston coupled to the armature and positioned within the piston channel, the piston having an outer surface facing an inner wall of the piston channel, an inlet end in fluid communication with the first fluid chamber, and an outlet end in fluid communication with the second fluid chamber, and the piston being moveable within the piston channel;
    at least one groove formed in the outer surface of the piston from the inlet end of the piston to the outlet end of the piston, the at least one groove forming a first flow path to conduct fluid between the first fluid chamber and the second fluid chamber; and
    an annulus defined between the outer surface of the piston and the inner wall of the piston channel, the annulus forming a second flow path to conduct fluid between the first fluid chamber and the second fluid chamber;
    wherein the at least one groove comprises a helical groove around the piston.

2. The actuator mechanism of claim 1, wherein the helical groove has a number of turns, a depth, a width, and a pitch that inhibits back leakage of fluid from the second fluid chamber to the first fluid chamber during movement of the armature from the refracted position to the forward position.

3. The actuator mechanism of claim 1, wherein the at least one groove comprises first and second oppositely wound helical grooves.

4. The actuator mechanism of claim 1, wherein the at least one groove comprises a plurality of substantially straight longitudinal grooves.

5. The actuator mechanism of claim 1, further comprising a valve assembly having a valve that seals the piston channel from the second fluid chamber when the armature is in the retracted position.

6. The actuator mechanism of claim 5, wherein the valve, the piston, and the piston channel together define a piston chamber when the armature is in the retracted position, the piston chamber storing fluid received from the first fluid chamber via the at least one groove.

7. The actuator mechanism of claim 6, wherein:
    movement of the armature from the refracted position to the forward position reduces volume of the piston chamber, and increases pressure within the piston chamber to open the valve such that the fluid stored in the piston chamber is discharged into the second fluid chamber, the at least one groove inhibiting back leakage of the fluid from the piston chamber during the movement of the actuator from the refracted position to the forward position; and
    movement of the armature from the forward position to the retracted position causes the valve to close, and creates negative pressure which draws the fluid from the first fluid chamber, through the at least one groove, and into the piston chamber for a next discharging operation.

* * * * *